United States Patent
Wang et al.

(10) Patent No.: US 11,834,524 B2
(45) Date of Patent: Dec. 5, 2023

(54) METHOD FOR PREPARING CHITIN HIGHLY DISPERSIBLE IN AQUEOUS PHASE AND CHITIN PREPARED THEREBY

(71) Applicant: Hangzhou Singclean Medical Products Co., Ltd, Zhejiang (CN)

(72) Inventors: Jue Wang, Zhejiang (CN); Yaru Wu, Zhejiang (CN); Meiqin Zhu, Zhejiang (CN)

(73) Assignee: Hangzhou Singclean Medical Products Co., Ltd, Hangzhou (CN)

( * ) Notice: Subject to any disclaimer, the term of this patent is extended or adjusted under 35 U.S.C. 154(b) by 0 days.

(21) Appl. No.: 17/828,152

(22) Filed: May 31, 2022

(65) Prior Publication Data
US 2023/0312763 A1  Oct. 5, 2023

(30) Foreign Application Priority Data
Mar. 30, 2022  (CN) .......................... 202210327510.4

(51) Int. Cl.
*C08B 37/00* (2006.01)
*C08B 37/08* (2006.01)
*A61K 8/73* (2006.01)
*A61K 47/36* (2006.01)

(52) U.S. Cl.
CPC .............. *C08B 37/003* (2013.01); *A61K 8/73* (2013.01); *A61K 47/36* (2013.01)

(58) Field of Classification Search
CPC .......... C08B 37/003; A61K 8/73; A61K 47/36
See application file for complete search history.

(56) References Cited

FOREIGN PATENT DOCUMENTS

| CN | 108310460 B | * | 8/2021 | ......... A61L 24/0031 |
| WO | WO-0206410 A1 | * | 1/2002 | ........... C09D 105/08 |

OTHER PUBLICATIONS

Miyashita et al ("Phase structure of chitin/poly (glycidyl methacrylate) composites synthesized by a solution coagulation/bulk polymerization method", Polymer, vol. 38, No. 25, pp. 6181-6187, 1997) (Year: 1997).*
Jue Wang et al., The effect of monosaccharides on self-assembly of benzenetricarboxamides, Chinese Chemical Letters 30 (2019) 587-591.

* cited by examiner

*Primary Examiner* — Shaojia A Jiang
*Assistant Examiner* — Everett White

(57) ABSTRACT

The application discloses a method for preparing chitin highly dispersible in aqueous phase and prepared chitin. After chitin is ground, dissolved, modified with glycidol and purified, a final product glycidol chitin is obtained. The glycidol chitin prepared according to this method has good solubility in purified water, and the concentration can reach 100 mg/mL, which is obviously different from common insoluble or poorly soluble chitin derivatives. Glycidol chitin may have a wide range of application prospects in biomedicine, cosmetics, absorbable materials, and other related aspects.

4 Claims, 2 Drawing Sheets

METHOD FOR PREPARING CHITIN HIGHLY DISPERSIBLE IN AQUEOUS PHASE AND CHITIN PREPARED THEREBY

CROSS-REFERENCE TO RELATED APPLICATION

The present application claims priority from Chinese Patent Application No. 202210327510.4 filed on Mar. 30, 2022, the contents of which are incorporated herein by reference in their entirety.

TECHNICAL FIELD

The present application relates to chitin highly dispersible in aqueous phase and a preparation method thereof.

BACKGROUND

Chitin is a class of natural linear polysaccharides with a repeated chemical unit of 2-acetylamino-(1,4)-β-glucose. Chitin shows a wide source from nature, mainly existing in the shells of fish, shrimps, crabs, and other animals and the cell walls of fungal organisms. Chitin is one of the natural macromolecules with the highest content in nature except cellulose, and is the most abundant nitrogen-containing organic compound. Chitin has many excellent properties, such as good biocompatibility, low immunogenicity, better hemostasis, and plays an important role in biomedicine, absorbable materials, and other related fields.

However, the solubility of chitin and its derivatives is poor, which is closely related to its molecular structure and chemical composition. The structure of chitin is a linear macromolecule, and the molecular chain is easy to aggregate tightly. The non-covalent interaction between chitin molecules can be fully exerted to form a poorly soluble or dense structure (such as chitin whiskers). Meanwhile, the repeated unit of chitin is glucose which is an amphiphilic structure (Chinese Chemical Letters 30 (2019) 587-591). Hydrophilic hydroxyl and hydrophobic carbon-hydrogen bonds are distributed on both sides of a glucose pyranose ring. The specific sequence of the hydroxyl and the carbon-hydrogen bonds makes a complicated non-covalent interaction between glucose. It is generally difficult for solvents to overcome the hydrophilic and hydrophobic effects of this alternating arrangement. It is difficult for the molecular solvation, leaving a poor solubility. In addition, the 2-position hydroxyl of glucose in chitin is substituted by acetylamino, and the hydrogen bonding interaction easily occurs between adjacent acetylamino. When the hydrogen bonding interaction occurs, the acetylamino becomes hydrophobic, thereby further reducing the solubility of chitin. In short, due to the linear structure of chitin and the complicated hydrophilic and hydrophobic interactions between molecules, the solubility of chitin is poor.

Compared with chitin, although the solubility of chitin derivatives has been improved to a certain extent, it is still poor. The modification of chitin with epoxy, halogenated hydrocarbon and other reagents can reduce the tightness of its molecular packing. The functional groups introduced after the modification can also improve the solvation of chitin to a certain extent. In general, a majority of chitin derivatives have poor solubility, and a few derivatives can be used as hydrogels with a mass fraction of 1% to 3%. Thus, it is difficult to achieve better dispersibility in the aqueous phase system.

SUMMARY

An objective of the application is to provide a method for preparing chitin highly dispersible in aqueous phase. Glycidol chitin prepared according to the method has good dispersibility in the aqueous phase, and has a wide range of application prospects in tissue engineering, cell culture, cosmetics, Class III medical devices, and other related aspects.

The application adopts the following technical solution: a method for preparing chitin highly dispersible in aqueous phase, wherein comprising the steps of:
(1) dissolving chitin statically in an alkaline solution at a low temperature to form a homogeneous stable aqueous phase solution of chitin;
(2) adding glycidol (2,3-epoxy-1-propanol) to the aqueous solution of chitin at a ratio followed by a reaction with stirring; and
(3) performing a simple treatment on the reaction system obtained in the step (2), and performing dialysis and freeze-drying to obtain glycidol chitin.

As a preferred solution, in the step (1), after adding to an alkaline aqueous solution, the resulting mixture is allowed to stand at 4° C. to −80° C. for 1-60 days. The alkaline aqueous solution is an inorganic base/organic base mixed aqueous solution system. The inorganic base can be one or several of lithium hydroxide, sodium hydroxide, potassium hydroxide and cesium hydroxide, and the mass fraction of the inorganic base in the alkaline aqueous solution is 1.5% to 25.5%. Urea is used as an organic base and the mass fraction of the organic base in the alkaline aqueous solution is 0.5% to 9.5%.

As a preferred solution, in the step (2), after adding the glycidol to the alkaline aqueous solution of chitin, the reaction with stirring is performed at 0° C.-40° C. for 1-14 days. The feeding ratio is: 1.00 g of chitin corresponds to 20-200 μL of glycidol.

As a preferred solution, in the step (3) the dialysis is performed after the reaction system is diluted by 1-20 times with purified water, and then dialysate is taken out. A pH value thereof is adjusted to 1-5 with sulfuric acid, hydrochloric acid, phosphoric acid or nitric acid, and then the dialysis and freeze-drying are performed.

Another objective of the application is to provide chitin highly dispersible in aqueous phase. To this end, the application adopts the following technical solution:

Glycidol chitin, wherein the glycidol chitin is chitin prepared according to the above preparation method.

The glycidol chitin product prepared by the application is a white spongy solid, which is easy to absorb moisture. According to an experiment of the application, 10 mg, 25 mg, 50 mg, and 100 mg of glycidol chitin are dispersed in 1 mL of purified water, and the 10 mg, 25 mg, and 50 mg samples are rapidly dissolved after shaking. Although the 100 mg sample is difficult to be dissolved rapidly, it can also form a homogeneous stable system after standing for 6 hours.

The glycidol chitin of the application has very high dispersibility in purified water. Compared with the previous modified chitin, the glycidol chitin can also reach a uniform stable dispersion state at a high concentration (100 mg/mL). This feature is obviously different from those of chitin derivatives such as hydroxypropyl chitin, hydroxyethyl chitin and the like. Chitin is a natural material with good biocompatibility. Small molecules such as sodium hydroxide, urea, unreacted glycidol, etc. in the system can all be removed by dialysis. The pH value of the aqueous solution of glycidol chitin is 7-8, which is in line with the pH range of a human body. Thus, it can be used in tissue engineering, cell culture, cosmetics, Class III medical devices, and other related fields.

The application will be further described below with reference to the accompanying drawings and examples.

DETAILED DESCRIPTION OF THE EMBODIMENTS

Figure 1:
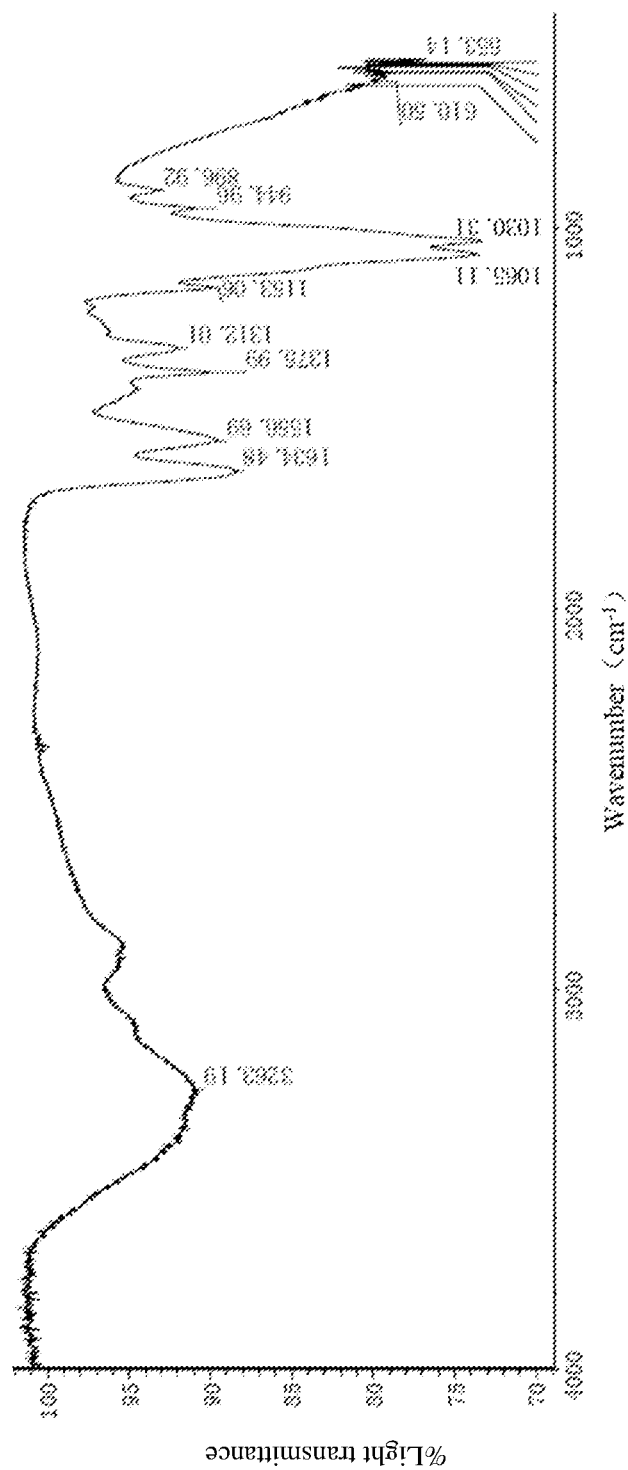
FIG. 1 is an infrared spectrogram of glycidol chitin prepared by the application.

In order to further understand the application, the method for preparing chitin highly dispersible in aqueous phase provided by the application will be described in detail below with reference to examples. However, the application is not limited to these examples, and non-essential improvements and adjustments made by those skilled in the art under the core guiding ideology of the application still fall into the protection scope of the application.

Example 1 Preparation of a Chitin Solution (1) Preparation of chitin powder. 20.00 g of chitin was weighed and placed into a traditional Chinese medicine grinder, and it was ground for 2 minutes. The ground chitin was taken out, and passed through 20-mesh and 50-mesh sieves in turn to obtain chitin powder.

(2) Preparation of an alkaline aqueous solution. 129.42 g of NaOH was accurately weighed, and was added slowly and repeatedly to 1 L of purified water. After the NaOH was completely dissolved and the temperature of the system dropped to normal temperature, 47.06 g of urea was added to the solution, and was stirred to be dissolved. The system was cooled to room temperature. In the alkaline aqueous solution, the mass fraction of the sodium hydroxide was 11.0%, the mass fraction of the urea was 4.0%, and the mass fraction of the purified water was 85%.

(3) Dissolution and dispersion of chitin powder. 2.00 g of the chitin powder was taken and added to 1 L of the alkaline aqueous solution, and it was stirred to be dispersed. The whole system was immersed in a −20° C. low temperature medium for 24 hours. After taken out, the system was returned to room temperature, and then was immersed in the −20° C. low temperature medium again. The system was allowed to stand for 16 days, and was returned to room temperature.

Example 2 Preparation of Glycidol Chitin

100 μL of glycidol was accurately measured and added to 50 mL of the chitin solution prepared in Example 1. The reaction with stirring was performed for 2 days.

Example 3 Preparation of Glycidol Chitin

300 μL of glycidol was accurately measured and added to 50 mL of the chitin solution prepared in Example 1. The reaction with stirring was performed for 5 days.

Example 4 Preparation of Glycidol Chitin

600 μL of glycidol was accurately measured and added to 50 mL of the chitin solution prepared in Example 1. The reaction with stirring was performed for 10 days.

Example 5 Purification of Glycidol Chitin 150 mL of purified water was added to the reaction system in Example 2 followed by stirring uniformly. The system was dialyzed in the purified water for 4 times, 1 day/time. The purified system was taken out, acidified to pH 1 with sulfuric acid, and then dialyzed in the purified water for 4 times, 1 day/time. Finally, freeze-drying was performed.

Chitin prepared in Examples 2-4 all has good water solubility. However, there are differences in the reaction system. When the glycidol was just added, the glycidol and the aqueous solution were in two phases. With the prolongation of the reaction time, the system of Example 2 tended to be clarified. The system of Example 3 was slightly cloudy. The system of Example 4 was obviously cloudy. By comprehensively considering the water solubility of the product, feeding, and other factors, the condition of Example 2 was comparatively good.

Figure 2:
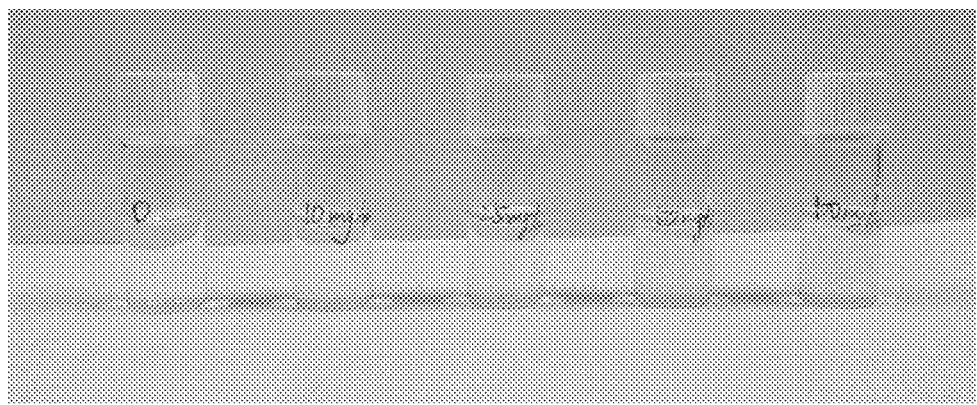
FIG. 2 is a picture showing dispersion effects of 10 mg, 25 mg, 50 mg, and 100 mg of glycidol chitin prepared by the application in purified water.
Figure 3:
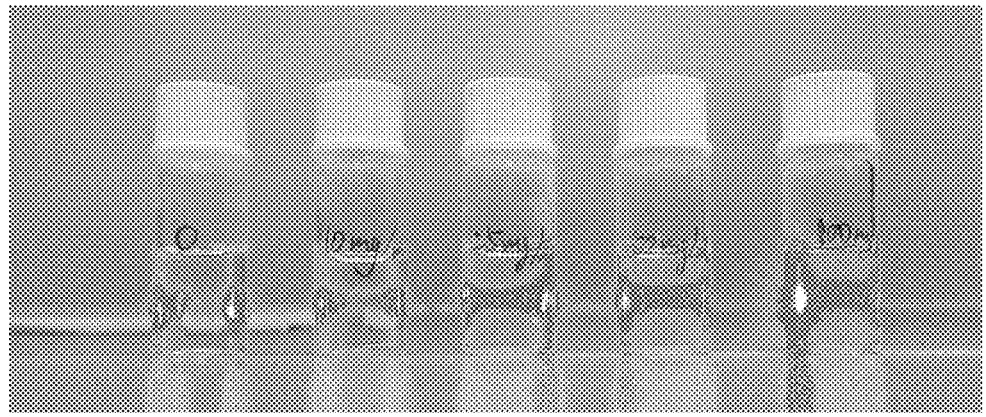
FIG. 3 is an effect picture of the Tyndall phenomenon of 10 mg, 25 mg, 50 mg, and 100 mg of glycidol chitin prepared by the application in purified water.

The infrared spectrograms of the glycidol chitin of Example 2, Example 3 and Example 4 are relatively similar, and the infrared spectrogram of Example 2 is shown in FIG. 1. The pH values of the 3% wt aqueous solutions of the products obtained in Example 2, Example 3, and Example 4 are 8.07, 8.00, and 7.88, respectively. 10 mg, 25 mg, 50 mg, and 100 mg of the glycidol chitin prepared in Example 2 were taken, and 1 mL of purified water was added, respectively. 10 mg, 25 mg, and 50 mg samples can be dispersed in purified water after shaking for 5 minutes. 100 mg of glycidol chitin was comparatively difficult to be dispersed quickly, and initially a hydrogel was formed. After standing at 4° C. overnight, a homogeneous stable transparent dispersion system was obtained. FIG. 2 indicates a picture showing the effects of 10 mg, 25 mg, 50 mg, and 100 mg glycidol chitin samples and a purified water blank sample. The Tyndall effects of the samples are shown in FIG. 3. With the increase of the sample concentration, the laser light path becomes more and more obvious.

It can be seen that the modification with a small amount of glycidol can significantly improve the water solubility of chitin, and the highest concentration can reach 100 mg/mL. The glycidol chitin prepared according to the method of the application has the original biocompatibility and degradability of chitin. The pH value of the aqueous solution of the glycidol chitin is 7-8, which is in line with the pH range of human physiological activities. Compared with chitin and most existing chitin derivatives, the glycidol chitin has excellent water solubility and good biological safety, and can be used in tissue engineering, cell culture, cosmetics, Class III medical devices, and other related fields.

The invention claimed is:
1. A method for preparing chitin dispersible in aqueous phase, wherein the method comprises steps of:
 (1) dissolving chitin statically in an alkaline solution at 4° C. to −80° C. to form a homogeneous stable aqueous phase solution of chitin;
 (2) adding glycidol to the aqueous phase solution of chitin at a ratio followed by a reaction with stirring; and
 (3) diluting a reaction mixture obtained from step (2) with purified water, and performing dialysis and freeze-drying to obtain glycidol chitin.

2. The method according to claim 1, wherein in the step (1), after adding chitin to the alkaline aqueous solution, allowing a resulting mixture to stand at 4° C. to −80° C. for 1-60 days.

3. The method according to claim 1, wherein in step (2), after adding the glycidol to the alkaline aqueous solution of chitin, performing the reaction with stirring at 0° C.-40° C. for 1-14 days.

4. The method according to claim 1, wherein in step (3), performing the dialysis after the reaction mixture being diluted by 1-20 times with purified water, then taking out a dialysate, adjusting a pH value thereof to 1-5 with sulfuric acid, hydrochloric acid, phosphoric acid or nitric acid, and then performing the dialysis and freeze-drying.

* * * * *